United States Patent [19]

Mixan et al.

[11] 4,199,581

[45] Apr. 22, 1980

[54] 1,4-DITHIINO PYRAZINE TETRACARBONITRILES

[75] Inventors: Craig E. Mixan; R. Garth Pews, both of Midland, Mich.

[73] Assignee: The Dow Chemical Company, Midland, Mich.

[21] Appl. No.: 944,669

[22] Filed: Sep. 22, 1978

[51] Int. Cl.$^2$ .................. C07D 495/04; C07D 495/14; A01N 9/12
[52] U.S. Cl. .................................... 424/250; 544/345; 544/350
[58] Field of Search ................. 544/345, 350; 424/250

[56] References Cited

U.S. PATENT DOCUMENTS

| | | | |
|---|---|---|---|
| 3,531,495 | 9/1970 | Burton et al. | 71/92 |
| 3,761,475 | 9/1973 | Kurihara et al. | 544/345 |
| 3,879,394 | 4/1975 | Donald | 544/409 |

Primary Examiner—Alton D. Rollins
Assistant Examiner—James H. Turnipseed

[57] ABSTRACT

Novel 1,4-Dithiinopyrazinetetracarbonitriles are disclosed. Their method of use in the control and kill of bacteria and fungi, and compositions containing the novel compounds as the active ingredients therein are claimed.

5 Claims, No Drawings

1,4-DITHIINO PYRAZINE TETRACARBONITRILES

SUMMARY OF THE INVENTION

The novel compounds of the present invention, hereinafter alternatively referred to as "active compounds", are 1,4-Dithiinopyrazinetetracarbonitriles, specifically 1,4-Dithiino(2,3-b)pyrazine-2,3,6,7-tetracarbonitrile (Compound 1), which corresponds to the formula

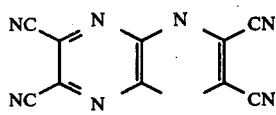

and 1,4-Dithiino(2,3-b) (5,6-b')dipyrazine-2,3,7,8-tetracarbonitrile (Compound 2), which corresponds to the formula

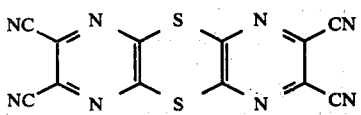

The active compounds, directly or as active ingredients in formulations and compositions, exhibit, in antimicrobially-effective amounts, antimicrobial activity against fungi and bacteria. Hereinafter the terms "antimicrobial" and "antimicrobially-effective", when used in conjunction with the active compounds, will be employed to identify their activity against fungi and/or bacteria.

Both Compound 1 and Compound 2 may be individually prepared by adding, 2,3-dichloro-5,6-dicyanopyrazine to disodium dimercaptomaleonitrile in dimethylformamide. To prepare Compound 1, the reaction mixture is maintained at about 20° C. to about 40° C., with agitation, until substantial formation of the desired product, usually from about 1 to about 8 hours. Upon completion of the reaction, the resulting product mass is poured into water, whereupon the desired crude solid product precipitates. The product compound is recovered by filtration, washed with water and dried and, if desired, can be further purified by conventional techniques known to those skilled in the art.

To prepare Compound 2, the reaction mixture is maintained at about 20° C. to about 60° C., with agitation, until substantial formation of the desired product, usually from about 48 to about 72 hours. Upon completion of the reaction, the resulting product mass is poured into water, whereupon the desired crude solid product precipitates. The product compound is recovered by filtration, washed with water and dried and, if desired, can be further purified by conventional techniques known to those skilled in the art. Alternatively, Compound 2 can be prepared by the reaction of 2,3-dichloro-5,6-dicyanopyrazine and sodium sulfide nonahydrate in dimethylformamide. The reaction mixture is maintained at about 20° C. to 60° C., with agitation, until substantial formation of the desired product, usually from about 4 to about 12 hours. The desired product compound may be recovered by the procedures set forth above.

Ordinarily, substantial equimolar proportions of the starting materials are employed in any of the above-described processes.

DESCRIPTION OF THE PREFERRED EMBODIMENTS

The following examples illustrate the present invention and the manner by which it can be practiced but as such should not be construed as limitations upon the overall scope of the same.

EXAMPLE 1

Preparation of Compound 1

To a stirred solution of 18.6 g (0.1 mol) of disodium dimercaptomaleonitrile in 200 ml of DMF was added 20 g (0.1 mol) of 2,3-dichloro-5,6-dicyanopyrazine in 150 ml of DMF. The reaction mixture was stirred at 35°–40° C. for 6 hrs and was thereafter poured into 1400 ml of water. The resulting precipitate was collected by suction filtration, washed with water, and dried. The crude product was dissolved in acetone/CHCl$_3$, decolorized with charcoal, and dried over MgSO$_4$. Two recrystallizations from CHCl$_3$ afforded 10.0 g (37% yield from the dicyanopyrazine) of yellow crystals, m.p. 201°–203° C.

A sample was subjected to elemental analysis. The results obtained were as follows:

Analysis for $C_{10}N_6S_2$: Calcd: C, 44.78; N, 31.34; S, 23.88. Found: C, 44.2; N, 31.71; S, 23.4.

The mass spectrum [(M.+) m/e=268] confirmed the assigned structure.

EXAMPLE 2

Preparation of Compound 2

To a stirred solution of 15 g (0.08 mol) of disodium dimercaptomaleonitrile in 150 ml of DMF, was gradually added 15 g (0.075 mol) of 2,3-dichloro-5,6-dicyanopyrazine in 100 ml of DMF. The reaction mixture was stirred at room temperature (~25° C.) for 72 hours and was thereafter poured into 1 liter of water. The resulting precipitate was collected by suction filtration, washed with water, and dried. The crude product was dissolved in acetone/CHCl$_3$, decolorized with charcoal, and dried over MgSO$_4$. Recrystallization from CHCl$_3$ afforded 5.0 g (42% yield from the dicyanopyrazine) of dark brown crystals, m. p. ~300° C. (decomposition).

A sample was subjected to elemental analysis. The results obtained were as follows:

Analysis for $C_{12}N_8S_2$: Calcd: C, 45.00; N, 35.00; S, 20.00. Found: C, 44,8; N, 35.35; S, 20.6.

The mass spectrum [(M.+) m/e=320] confirmed the assigned structure.

The active compounds of the invention are suitable for use an antimicrobials for the control of bacteria and fungi. This is not to suggest that the active compounds and mixtures thereof with usual additives are equally effective against all such organisms at the same concentration. The active compounds can be employed in an unmodified form or dispersed on a finely divided solid and employed as a dust. Such mixtures can also be dispersed in water with the aid of a surface-active agent and the resulting emulsion employed as a spray. In other procedures, the active compounds can be employed as the active constituents in solvent solutions, oil-in-water or water-in-oil emulsions. The augmented compositions are adapted to be formulated as concentrates and subsequently diluted with additional liquid or solid adjuvants to produce the ultimate treating compositions. Good control and kill have been realized against a number of representative organisms with compositions wherein antimicrobially-effective amounts of from about 50 to about 500 parts by weight of one or more of the active compounds per million parts of such compositions are employed. As stated hereinbefore the active antimicrobially-effective amount to be employed against a given organism or in a certain composition can readily be determined by one skilled in the art.

Incorporation of the active compounds of this invention into materials which are subject to fungal attack inhibits the growth of the fungi and preserves the original value of the materials. The active compounds are sufficiently nonvolatile and water-insoluble so that they will persist on or in such materials for long periods of time. Examples of materials which are adversely affected by fungal growth are latex and alkyl paint films, wood and wooden products. The active compounds are sufficiently active against fungi such that only small quantities are required to prevent mildew on paint films or wood rot. The active compounds are therefore useful for a long-term protection against fungal growth in or on materials having a wood basis or a protective or decorative paint film or other coating or covering subject to fungal attack.

In a standard activity test, samples of Compound 1 and Compound 2 were individually dispersed in warm melted nutrient agar which was poured into petri dishes and allowed to solidify, the active compounds being employed in an amount sufficient to provide from 10 to 500 parts by weight thereof per million parts (ppm) of the ultimate agar composition. The surface of the agar was inoculated with a variety of bacterial and fungal pest organisms, and the inoculated plates incubated under conditions conducive to bacterial and fungal growth. Similar check plates in which the agar did not contain the active compounds or other toxic compounds were similarly inoculated and incubated.

In these studies, Compounds 1 and 2 gave 100% growth inhibition (kill) and control of the following organisims, as set forth in the Table, at the indicated concentrations in parts per million (ppm):

TABLE

| Organism | Antimicrobial Activity Concentration in ppm | |
|---|---|---|
| | Compound 1 | Compound 2 |
| S. aureus | 50 | 50 |
| S. typhosa | 500 | 100 |
| A. niger | 100 | 50 |
| A. Fumigatus | 50 | 50 |
| C. pelliculosa | 50 | 50 |
| C. albicans N | 100 | 500 |
| C. albicans D | 100 | 100 |
| B. subtilis | 50 | 10 |
| A. aerogenes | 500 | 500 |
| P. aeruginosa | 500 | 500 |
| E. coli | 500 | 500 |
| S. marcesens | 500 | 500 |
| T. sp. med. col. VI | 100 | 500 |
| C. ips | 50 | 50 |
| T. mentagrophytes | 50 | 50 |
| P. chrysogesum | 50 | 50 |
| P. pullulans | 100 | 50 |

Preparation of the Starting Material 2,3-dichloro-5,6-dicyanopyrazine may be prepared according to the process taught in U.S. Pat. No. 3,879,394.

What is claimed is:

1. A compound selected from the group consisting of 1,4-dithiino(2,3-b)pyrazine-2,3,6,7-tetracarbonitrile and 1,4-dithiino(2,3-b) (5,6-b')dipyrazine-2,3,7,8-tetracarbonitrile.

2. The compound of claim 1 which is 1,4-dithiino(2,3-b)pyrazine-2,3,6,7-tetracarbonitrile.

3. The compound of claim 1 which is 1,4-dithiino(2,3-b) (5,6-b'')dipyrazine-2,3,7,8-tetracarbonitrile.

4. A method for controlling bacteria and fungi which comprises applying to said bacteria and fungi or their habitat an antimicrobially-effective amount of a compound of claim 1.

5. A composition for controlling bacteria and fungi comprising an antimicrobially-effective amount of a compound of claim 1 in combination with a solid or liquid diluent medium.

* * * * *